United States Patent [19]

Ferguson et al.

[11] 4,228,299
[45] Oct. 14, 1980

[54] CHEMICAL PROCESS FOR PREPARING ALKYL ESTERS OR THE AMIDE OF 3-(β,β-DIHALOVINYL)-2,2-DIMETHYLCYCLOPROPANE -CARBOXYLIC ACID

[75] Inventors: Ian Ferguson; Robert J. Lindsay, both of Manchester, England

[73] Assignee: Imperial Chemical Industries Limited, London, England

[21] Appl. No.: 852,557

[22] Filed: Nov. 17, 1977

[30] Foreign Application Priority Data

Nov. 18, 1976 [GB] United Kingdom ............... 48078/76
May 25, 1977 [GB] United Kingdom ............... 22046/77

[51] Int. Cl.$^2$ ..................... C07C 102/08; C07C 67/22
[52] U.S. Cl. .................................. 560/124; 260/464; 260/453 RW; 260/557 R; 562/506
[58] Field of Search ................ 260/514 H, 557 R; 560/124

[56] References Cited

U.S. PATENT DOCUMENTS 3,658,879  4/1972  Julia ..................................... 560/124
4,000,180  12/1976  Punja .................................... 560/124

FOREIGN PATENT DOCUMENTS 2547510  4/1976  Fed. Rep. of Germany ........... 560/124
2621830  11/1976  Fed. Rep. of Germany ........... 560/124
2621832  11/1976  Fed. Rep. of Germany ........... 560/124
52-14750  3/1977  Japan ..................................... 560/124
7605172  11/1976  Netherlands ........................... 560/124

OTHER PUBLICATIONS

Zil'berman, Russian Chemical Reviews, vol. 31, pp. 615-633 (1962).

*Primary Examiner*—Natalie Trousof
*Assistant Examiner*—Michael C. Shippen
*Attorney, Agent, or Firm*—Cushman, Darby & Cushman

[57] ABSTRACT

Process for the preparation of 1-lower alkoxycarbonyl-3-(β,β-dichlorovinyl)-2,2-dimethylcyclopropanes from the corresponding 1-cyano-1-carboxylic acid ester by hydrolysis, decarboxylation of the free carboxylic acid, reaction of the cyclopropane nitrile with a lower aliphatic alcohol and anhydrous hydrogen chloride, followed by alcoholysis or hydrolysis of the reaction product so obtained to give the desired ester or carboxylic acid. Includes a method for the separation of essentially pure cis- and trans-isomers from the mixed nitriles. The products are useful intermediates for the preparation of pyrethroid insecticides.

2 Claims, No Drawings

CHEMICAL PROCESS FOR PREPARING ALKYL ESTERS OR THE AMIDE OF 3-(β,β-DIHALOVINYL)-2,2-DIMETHYLCYCLOPROPANE -CARBOXYLIC ACID

This invention relates to a chemical process and more particularly to a process for the preparation of certain cyclopropane derivatives which are valuable as intermediates in the manufacture of insecticides.

Esters, such as the m-phenoxybenzyl ester, of 3-β,β-dichlorovinyl-2,2-dimethylcyclopropane carboxylic acid (I)

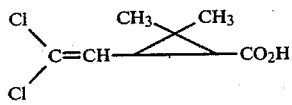

are valuable insecticides.

The preparation of the acid (I) has been described by Farkas et al (Collection Czechoslov. Chem. Commun., 24, 2230–2236 (1959)) by the reaction of ethyl diazoacetate with 1,1-dichloro-4-methyl-1,3-pentadiene followed by hydrolysis of the resulting ethyl ester. This process is not suitable for large scale preparation of the acid because of the difficulties of working with ethyl diazoacetate, which is a substance which can decompose explosively unless the conditions are rigorously controlled, and which is believed to be a potent carcinogen.

It has now been found that lower alkyl esters of the acid (I) and its corresponding dibromo analogue may be prepared by a route which avoids the use of diazoacetic esters.

According to the present invention there is provided a process for the preparation of a compound of the formula:

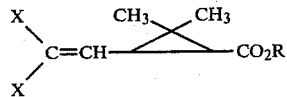

wherein R represents a hydrogen atom or a lower alkyl group and X represents a chlorine atom or a bromine atom which comprises:

(a) the step of alkaline hydrolysis of a cyclopropane carboxylic ester of the formula:

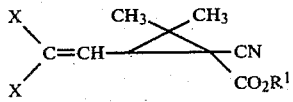

wherein $R^1$ has the same meaning as R and may be the same or different, and X has the meaning defined above, (b) the step of decarboxylation of the compound of formula:

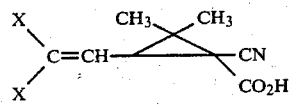

obtained in step (a) by heating the compound in a polar aprotic solvent, (c) the step of treating the compound of formula:

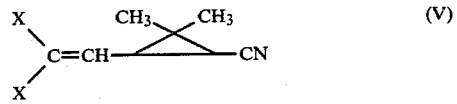

obtained in step (b) with dry hydrogen chloride in an alcohol R.OH, wherein R has the meaning defined above, the reaction occurring either with concurrent alcoholysis or being followed by a hydrolysis step whereby a carboxylic acid ester or carboxylic acid of formula (II) is obtained. Each individual step, and the two combinations of successive steps, are also features of the invention.

The alkaline hydrolysis step (a) may be carried out by heating the cyanocyclopropane carboxylic ester in aqueous alcoholic solution with a slight excess over the theoretical amount (for example, up to about 1.3 moles per mole of ester) of caustic alkali necessary to effect hydrolysis. The aqueous alcoholic solution is conveniently aqueous ethanol. The caustic alkali may be potassium hydroxide and is preferably sodium hydroxide. The hydrolysis is conveniently carried out at the reflux temperature of the aqueous alcoholic medium. A reaction time of about 3 hours is usually sufficient to complete the hydrolysis under these conditions. The free carboxylic acid may be isolated from the reaction mixture by acidification to a pH of about 2. Examples of acids which may be used for this purpose are dilute hydrochloric acid and dilute sulphuric acid. Water is added to the acidified mixture prior to filtration or alternatively the solution is diluted before acidification. The carboxylic acid precipitates from the solution and is collected. The cyclopropane carboxylic acid is washed free from the acid used to precipitate it from solution, and dried at a moderate temperature, for example, up to about 60° C. The carboxylic acid is generally obtained in essentially theoretical yield from the ester starting material.

Decarboxylation of the cyanocyclopropane carboxylic acid (step (b)) obtained from the preceding stage may be effected by heating the acid in a polar aprotic solvent having a boiling point greater than 150° C. Suitable polar aprotic solvents which may be used are, for example, dimethylformamide, dimethylacetamide and dimethylsulphoxide. It is preferred that the decarboxylation reaction should be carried out under an inert atmosphere, for example, nitrogen. The reaction is conveniently conducted at the reflux temperature of the aprotic solvent.

Decarboxylation is in general facilitated and yield of nitrile improved by carrying out the reaction in the pesence of a copper salt, and preferably also in the presence of water. Examples of the copper salts which can be used are copper (II) sulphate, copper (II) chloride, copper (II) acetate and copper (I) chloride. The amount of copper salt which is used is preferably from 1 to 10% by weight based on the weight of cyanoacid, and the amount of water is conveniently approximately 2 moles per mole of cyanoacid. Reaction times in the range 0.5 to 10 hours may be employed, in general a reaction time of 4 to 8 hours is adequate. The decarboxylation product may be isolated by distilling off the solvent under reduced pressure, if necessary after a preliminary filtration of the solution, followed by high vacuum distillation of the cyanocyclopropane derivative.

The product obtained as a result of carrying out step (c) is, at least initially, the iminoether hydrochloride of formula:

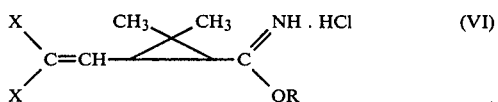

Compounds of formulae (I) to (VI) exist in two isomeric cis- and trans-forms, according to whether the dihalogenovinyl group in the 3-position and the —CO$_2$R, —CO$_2$R$^1$, —CO$_2$H, —CN or —C(OR)=NH.HCl group in the 1-position are on the same side (cis) or opposite sides (trans) of the cyclopropane ring.

As obtained by normal methods of preparation the nitrile (V) consists of a mixture of cis- and trans-isomers, and it has further been found that reaction of nitrile (V) with an alcohol R.OH and anhydrous hydrogen chloride does not proceed with equal ease for both isomers. The trans-isomer of (V) can react preferentially to give trans-(VI) leaving cis-(V) substantially unchanged. The trans-(VI) and cis-(V) may readily be separated, and the trans-(VI) may then be converted into the corresponding trans acid or ester (II), according to whether the group R is a hydrogen atom or a lower alkyl group. The cis-(V) may then be reacted with the alcohol R.OH and anhydrous hydrogen chloride under more vigorous conditions to give cis-(VI) which may then be converted into cis-(II).

The cis-isomers of insecticidal esters of cyclopropanecarboxylic acids of formula (II) in which R=H are more potent insecticides than the corresponding trans-isomers, and consequently it is desirable to obtain the cis-isomer of the compound (II) in as pure a form as possible so that it may subsequently be converted into an insectidical (e.g. m-phenoxybenzyl) cis-ester substantially free from less active trans-isomer.

Thus, the product which is obtained as a result of carrying out step (c) of the above reaction sequence depends upon the reaction conditions. If it is desired to separate the cis- and trans-isomers of (VI) step (c) is carried out at a temperature at which the cis-nitrile (V) is left substantially unreacted. Preferably the temperature does not exceed 50° C. The reaction of mixed cis- and trans-nitriles (V) with alcohol R.OH and anhydrous hydrogen chloride is conveniently continued until the reaction mixture is saturated with hydrogen chloride. The mixture is then conveniently stirred for a further period, for example, up to 18 hours, to ensure completion of the reaction of the trans-nitrile (V). The reaction mixture, consisting essentially of trans-iminoether hydrochloride (VI) in admixture with unreacted cis-nitrile (V), is then treated with water, preferably by pouring the mixture into crushed ice/water. The soluble trans-iminoether hydrochloride dissolves, leaving the insoluble cis-nitrile which is separated from the aqueous solution by extraction with a suitable water-immiscible inert solvent, for example, toluene. Removal of the solvent, conveniently under reduced pressure, leaves the cis-nitrile, which is then reacted with an essentially anhydrous alcohol R.OH and anhydrous hydrogen chloride under conditions more vigorous than those under which the trans-nitrile reacts.

Preferably the cis-nitrile is dissolved in the anhydrous lower alcohol R.OH and the solution is saturated with dry hydrogen chloride at the reflux temperature of the mixture until all of the cis-nitrile has reacted, a process which may take up to 36 hours to complete. During the reaction of the cis-nitrile with alcohol R.OH and hydrogen chloride at an elevated temperature, the iminoether hydrochloride which is formed may undergo further reaction whereby it is converted into a mixture of the desired cis-ester (II) and the corresponding cis-amide, without addition of water to the reaction mixture.

This cis-ester/amide product may be converted entirely into cis-ester, by mixing it with more of the alcohol R.OH, a strong mineral acid, preferably concentrated hydrochloric acid, and water, and heating the mixture, preferably under reflux, to convert the amide into ester, the ester which is already present being unchanged under these conditions. The cis-ester essentially free from amide which is thus obtained may be recovered by extracting it from the reaction mixture with an inert water-immiscible solvent such as toluene, the solvent that being removed by conventional means, e.g. evaporation or distillation, to give the desired cis-ester.

Alternatively, the cis-ester/amide reaction mixture may be converted into the corresponding free carboxylic acid by drowning the mixture into water, extracting with toluene, removing the toluene by distillation, preferably under reduced pressure and then heating the residual product with water and a strong mineral acid, preferably hydrochloric acid, conveniently under reflux, in order to effect hydrolysis of the ester and amide to the free carboxylic acid. Hydrolysis may be carried out under these conditions for up to 24 hours in order to ensure completion of the reaction. After cooling the reaction mixture it is extracted with toluene. The toluene extract is washed with dilute aqueous alkali, for example, a 5% w/w aqueous solution of sodium hydroxide, the toluene is discarded and the aqueous alkaline washings are acidified, for example, with hydrochloric acid. The free carboxylic acid separates and is collected.

The aqueous solution of trans-iminoether hydrochloride which is obtained after the first, low temperature, reaction of the mixed cis- and trans-nitriles (V) with dry hydrogen chloride and alcohol R.OH, may be heated, conveniently to reflux temperature, to convert the iminoether hydrochloride into the corresponding trans-ester (II) which may be isolated from the aqueous mixture in a similar manner to the described for the cis-ester.

By the term "lower alkyl" throughout this specification we mean an alkyl group containing from 1 to 4 carbon atoms, for example, methyl, ethyl, n-propyl, isopropyl, n-butyl, sec-butyl or isobutyl.

Essentially anhydrous lower alcohols for use in the iminoether hydrochloride stages of the present process may if desired be obtained from alcohols which contain traces of moisture by the addition to the alcohol of sufficient thionyl chloride to combine with the water.

It will be understood that if step (c) is carried out from the start at a temperature high enough for the cis-nitrile (V) to react, then the trans-nitrile (V) will also react, and the product obtained will be a mixture of cis- and trans-esters or acids (II)

It is known that the alkoxycarbonyl group can be removed from a compound of the formula:

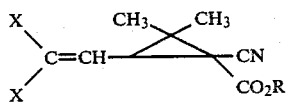

by heating the compound in a polar aprotic solvent in the presence of an alkali metal halide or cyanide and water to give the nitrile having the formula:

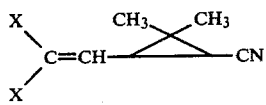

wherein R and X have the previously defined meanings, without going through the intermediate cyano acid of the formula:

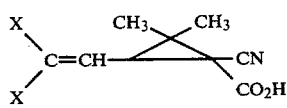

This is a known process.

The present process, in which the cyanoester is first hydrolysed to give the cyano acid, followed by decarboxylation of the latter, has certain advantages over the direct dealkoxycarbonylation route, namely, a higher overall yield, shorter reaction times, milder reaction conditions and the opportunity of purifying the intermediate cyano acid by simple chemical means. The direct removal of the —COOR group under the conditions described in the above applications generally gives a mixture of the desired cyclopropane nitrile and ring-opened nitrile. The present process gives essentially the desired cyclopropane nitrile.

The starting material for the present process, that is, the compound of the formula:

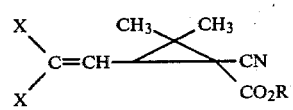

wherein R and X have the previously defined meanings, may be obtained by reaction of 1,1-dichloro(or dibromo)-4-methylpenta-1,3-diene with an alkyl cyanoacetate in the presence of cupric acetate/cupric chloride/lithium chloride and in a lower alkyl acetate, for example, ethyl acetate or butyl acetate, as solvent.

The invention is illustrated but not limited by the following Examples, in which parts and percentages are by weight.

EXAMPLE 1

(a) Alkaline hydrolysis of ethyl 1-cyano-3-($\beta,\beta$-dichlorovinyl)-2,2-dimethylcyclopropane-1-carboxylate The above compound (1.0 mol) was heated to reflux (84° C.) in a mixture of 2 M aqueous sodium hydroxide (1.38 moles) and 1:1 aqueous ethanol. After 3 hours at reflux temperature the reaction mixture was cooled to 20° C. and 3 N-sulphuric acid was added to lower the pH of the mixture to 2. 1-Cyano-3-($\beta,\beta$-dichlorovinyl)-2,2-dimethylcyclopropane-1-carboxylic acid was precipitated. A further quantity of water was added to the mixture to complete the precipitation. The product was filtered off, washed with water until the washings no longer gave an acid reaction with Congo Red paper, and dried in an oven at 50°–60° C. The yield of carboxylic acid was 100%.

(b) Decarboxylation of 1-cyano-3-($\beta,\beta$-dichlorovinyl)-2,2-dimethylcyclopropane-1-carboxylic acid A 31.2% w/v solution of the carboxylic acid, obtained as described in (a) above (1.0 ml), in N,N-dimethylformamide was heated to reflux (145° C.). The reaction was carried out under an atmosphere of nitrogen. After 4 hours at reflux temperature the reaction mixture was cooled. The solution was concentrated by distilling off the solvent under reduced pressure. The product, 1-cyano-3-($\beta,\beta$-dichlorovinyl)-2,2-dimethylcyclopropane, was isolated from the residue by distillation under greatly reduced pressure and formed the fraction having a boiling range of 65°–72° C. at 0.06 mm/Hg pressure. The yield was approximately 55%.

(c) Hydrolysis of 1-cyano-3-($\beta,\beta$-dichlorovinyl)-2,2-dimethylcyclopropane A 39.5% w/v solution of the above compound, obtained as described in (b) above, in absolute ethanol was cooled to 0°–5° C. by external cooling and saturated with anhydrous hydrogen chloride. The mixture was stirred for 16 hours at room temperature and then drowned into ice and water. The resulting 2-phase mixture was extracted with toluene to remove unreacted cyano compound. The aqueous layer was heated to reflux temperature and maintained at this temperature for 30 minutes to ensure complete hydrolysis of the dissolved intermediate product, after which it was cooled and extracted with toluene. The toluene was removed from the extract by evaporation under reduced pressure. The residual oil contained 80% of ethyl 3-($\beta,\beta$-dichlorovinyl)-2,2-dimethylcyclopropane-1-carboxylate, as estimated by gas-liquid chromatographic analysis, the yield being approximately 35% based on the weight of starting material charged or 85% on the weight of starting material reacted, i.e. the amount charged less that recovered in the first toluene extraction.

EXAMPLE 2

Absolute ethanol (or technical grade dry ethanol to which a small amount of thionyl chloride has been added) (62 parts) and 1-cyano-3-($\beta,\beta$-dichlorovinyl)-2,2-dimethylcyclopropane (16.7 parts; 94% strength; cis:trans, 60:40) are charged to a reaction vessel fitted with an agitator, thermometer, condenser and gas inlet tube. The reaction mixture is cooled to 0° C. and dry hydrogen chloride is bubbled in until the solution appears to be saturated, whilst keeping the temperature of the reaction mixture below 5° C. by external cooling. This operation takes approximately 3 hours. The reaction mixture is then stirred below 5° C. for a further 12 hours, after which time all of the trans-nitrile appears to have reacted.

At the end of the reaction period the solution is drowned into a stirred mixture of crushed ice and water (200 parts) and stirred for 10 minutes. Toluene (43 parts) is added and after stirring the mixture for 5 minutes the toluene and aqueous layers are allowed to settle and then separated. The toluene layer, which contains unreacted cis-nitrile, is evaporated under reduced pressure to give 9.2 parts of a light-coloured oil. GLC analysis showed this to be essentially cis-nitrile.

The water layer is heated under reflux for 1 hour, cooled and extracted with toluene (43 parts). After separating the toluene layer from the aqueous solution the toluene is evaporated under reduced pressure to give 8 parts of a product comprising 70.5% trans-1-ethoxycarbonyl-3-($\beta,\beta$-dichlorovinyl)-2,2-dimethylcyclopropane and 5.7% of the corresponding cis-isomer.

The 9.2 parts of unreacted cis-nitrile recovered from the first stage are dissolved in absolute ethanol (or technical grade dry ethanol+thionyl chloride) (39 parts). The solution is heated with agitation to reflux temperature and dry hydrogen chloride is passed continuously through the refluxing solution for 36 hours, after which time all of the cis-nitrile appeared to have reacted.

The solution is cooled and drowned into a stirred mixture of ice and water (125 parts). The drown-out mixture is extracted with toluene (2×43 parts) and the toluene extract is evaporated under reduced pressure to give 10.9 parts of a product comprising 73% of cis-1-ethoxycarbonyl-3-($\beta,\beta$-dichlorovinyl)-2,2-dimethylcyclopropane and 1% of the corresponding trans-isomer, as a light coloured oil.

The combined yield of cis- and trans-esters based on the mixed nitrile starting material is 72%.

EXAMPLE 3

This is a comparative Example, and illustrates the improvement in yield obtained in decarboxylation step (b) when the reaction is carried out in the presence of a copper salt.

1-Cyano-3-($\beta,\beta$-dichlorovinyl)-2,2-dimethylcyclopropane-1-carboxylic acid (23.4 parts; 82.6% strength), dimethylformamide (70 parts), copper (II) sulphate pentahydrate (2.34 parts) and water (3.6 parts) are heated to reflux temperature (130° C.) under nitrogen and maintained at this temperature for 3 hours. The reaction mixture is worked up as described in paragraph (b) of Example 1. Alternatively it may be worked up by drowning into water (200 parts) and extracting the aqueous mixture with toluene (3×100 ml), the toluene then being evaporated off from the extract under reduced pressure to give the crude nitrile as 18.83 parts of a drak mobile oil, strength 70.2% by gas liquid chromatographic analysis. This yield corresponds to 84.2% at 100% strength on the cyanoacid starting material. The product can be obtained in purer form by distillation under reduced pressure as described in paragraph (b) of Example 1.

Further examples of the use of copper salts, with or without the addition of water, are given in the following Table. In each case the reaction was carried out as described above, on the same scale, and using dimethylformamide as the solvent:

| Copper salt | Reaction temperature (°C.) | Reaction time (hours) | Yield of nitrile (%) |
|---|---|---|---|
| None No added water | 150 | 6 | 58.0 |
| CuSO$_4$ . 5H$_2$O Water added | 130 | 3 | 84.2 |
| CuCl$_2$ 2H$_2$O Water added | 138 | 4 | 82.0 |
| CuCl Water added | 135 | 4 | 85.5 |
| Cu(OOCCH$_3$)$_2$ . H$_2$O Water added | 130 | 4 | 82.5 |
| CuSO$_4$ . 5H$_2$O No added water | 140 | 6 | 79.7 |
| CuCl$_2$ . 2H$_2$O No added water | 150 | 6 | 80.4 |

In the above preparations all the copper salts were used at 10% by weight on the weight of cyanoacid and the water, where added, was present at 2 moles per mole of cyanoacid.

The use of only 1% of any one of the above copper salts also results in a considerable improvement in yield of nitrile.

The use of dimethylacetamide in place of dimethylformamide as solvent gives similar results.

EXAMPLE 4

(a) Reaction of 1-cyano-3-($\beta,\beta$-dichlorovinyl)-2,2-dimethylcyclopropane with ethanol and hydrogen chloride.

Technical grade ethanol (44 parts) thionyl chloride (1.6 parts) and 1-cyan-3-($\beta,\beta$-dichlorovinyl)-2,2-dimethylcyclopropane (20 parts; 70% strength, cis-trans ratio 50:50) are charged to a reaction vessel fitted with an agitator, thermometer, condenser and gas inlet tube,. The reaction mixture is heated to reflux and dry hydrogen chloride is bubbled through the refluxing solution for 24 hours to complete the reaction. The product at this stage is a mixture of the required ester and the corresponding amide, formed by the cleavage of the intermediate iminoether hydrochloride.

(b) Preparation of Ethyl 3-($\beta,\beta$-dichlorovinyl)-2-2-dimethylcyclopropanecarboxylate Water (36 parts) ethanol (40 parts) and hydrochloric acid (30.5 parts 36° TW) are added to the reaction mixture obtained as described above, and the mixture stirred at reflux temperature for 24 hours. At the end of this reaction period the mixture is cooled and the product is extracted with toluene (100 parts). After separation of the toluene layer the toluene is evaporated off under reduced pressure to give 18.6 parts of a product comprising 44% of the trans-ester and 31% of the cis-ester. The overall yield is 80% based on nitrile charged.

If the 40 parts of ethanol are replaced by equivalent amounts of methanol, isopropanol or n-butanol, the corresponding methyl, isopropyl or n-butyl esters are similarly obtained.

(c) Preparation of 3-($\beta,\beta$-dichlorovinyl)-2,2-dimethylcyclopropanecarboxylic acid 15 parts of an ester/amide mixture (obtained as described in paragraph (a) above and isolated by drowning the reaction mass into water, extracting with toluene and evaporating the toluene under reduced pressure) are added to water (75 parts) and hydrochloric acid (75 parts; 36° TW). The mixture is refluxed for 24 hours, cooled and the product is extracted with toluene (50 parts). The toluene layer is separated and then washed with dilute alkali (50 parts of 5% NaCH). The toluene layer is discarded and the aqueous layer is acidified with hydrochloric acid (10 parts). The precipitated acid is collected by filtration and dried to give 5 parts of product.

Our copending United States patent application Ser. No. 852,556, filed Sept. 17, 1977, now abandoned, relates to a process for the preparation of 1-lower alkoxycarbonyl-3-(β,β-dichlorovinyl)-2,2-dimethylcyclopropane and 3-(β,β-dichlorovinyl)-2,2-dimethylcyclopropane-1-carboxylic acid from the corresponding 1-cyanocyclopropane-1-carboxylic acid ester by hydrolysis, decarboxylation of the free carboxylic acid to give the corresponding 1-cyanocyclopropane, reaction of the latter with a lower aliphatic alcohol and anhydrous hydrogen chloride at an elevated temperature to give a mixture of the desired ester and the corresponding amide, and converting the mixture of ester and amide into ester essentially free from amide by treating the mixture with more of the lower aliphatic alcohol, a strong mineral acid and water, or converting the mixture of ester and amide into the corresponding carboxylic acid by treating the mixture with water and a strong mineral acid, and isolating the ester or the carboxylic acid respectively so obtained.

We claim:

1. A process for the preparation of a mixture of essentially cis-ester and amide compound of the formula:

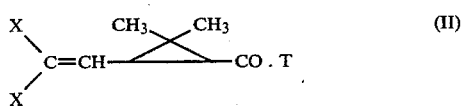

wherein T represents —$NH_2$ or the group OR in which R is a lower alkyl group and X represents a chlorine atom or a bromine atom, which comprises treating a mixture of cis- and trans-nitrile of formula:

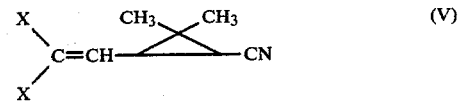

wherein X has the meaning stated above, with dry hydrogen chloride and an alcohol R.OH, wherein R has the meaning stated above, at a temperature at which only the trans-nitrile reacts, the cis-nitrile being left substantially unreacted, separating the unreacted cis-nitrile from the reaction mixture, followed by reaction of the cis-nitrile at an elevated temperature with dry hydrogen chloride and an essentially anhydrous alcohol R.OH and isolating from the reaction product the mixture of essentially cis- ester and amide compounds of formula (II).

2. A process for the preparation of an essentially trans-ester of the formula:

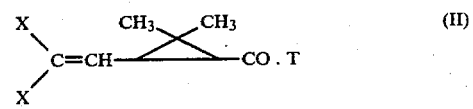

wherein T represents the group OR in which R is a lower alkyl group and X represents a chlorine atom or a bromine atom, which comprises treating a mixture of cis- and trans-nitriles of formula:

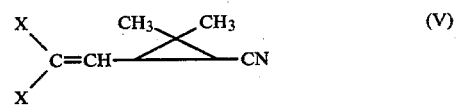

wherein X has the meaning stated above, with dry hydrogen chloride and an alcohol R.OH, wherein R has the meaning stated above, at a temperature at which only the trans-nitrile reacts, the cis-nitrile being left substantially unreacted, separating the unreacted cis-nitrile from the reaction mixture, mixing the reaction mixture, from which the cis-nitrile has been separated, with water, heating the aqueous mixture to effect conversion of the initial reaction product into the corresponding trans-ester, followed by isolation of the trans-ester from the reaction mixture.

* * * * *